United States Patent [19]

Petrillo, Jr. et al.

[11] 4,284,561

[45] Aug. 18, 1981

[54] HYDROXAMIC ACID DERIVATIVES OF MERCAPTOACYL AMINO ACIDS

[75] Inventors: Edward W. Petrillo, Jr., Pennington; Miguel A. Ondetti, Princeton, both of N.J.

[73] Assignee: E. R. Squibb & Sons, Inc., Princeton, N.J.

[21] Appl. No.: 99,382

[22] Filed: Dec. 3, 1979

[51] Int. Cl.³ .................. C07D 207/08; C07D 277/06; A61K 31/40; A61K 31/425
[52] U.S. Cl. .......................... 260/326.2; 260/326.35; 260/326.36; 260/326.43; 260/326.47; 424/270; 424/274; 548/200
[58] Field of Search ........... 260/326.43, 326.2, 326.35, 260/326.36, 326.47

[56] References Cited

U.S. PATENT DOCUMENTS

| | | | |
|---|---|---|---|
| 4,046,889 | 9/1977 | Ondetti et al. | 260/326.47 |
| 4,105,776 | 8/1978 | Ondetti et al. | 260/326.2 |
| 4,129,566 | 12/1978 | Ondetti et al. | 260/326.2 |
| 4,154,840 | 5/1979 | Ondetti et al. | 546/188 |
| 4,154,935 | 5/1979 | Ondetti et al. | 260/326.2 |
| 4,154,942 | 5/1979 | Ondetti et al. | 260/326.46 |

FOREIGN PATENT DOCUMENTS 861454 6/1978 Belgium .
2014132 8/1979 United Kingdom .

*Primary Examiner*—Donald G. Daus
*Assistant Examiner*—M. C. Eakin
*Attorney, Agent, or Firm*—Lawrence S. Levinson; Donald J. Barrack

[57] ABSTRACT

Hydroxamic acid derivatives of certain mercaptoacyl amino acids inhibit the conversion of angiotensin I to angiotensin II in mammals and are useful for the treatment of hypertension.

19 Claims, No Drawings

HYDROXAMIC ACID DERIVATIVES OF MERCAPTOACYL AMINO ACIDS

BACKGROUND OF THE INVENTION

U.S. Pat. No. 4,105,776, issued Aug. 8, 1979, discloses, inter alia, amides of certain mercaptoacyl amino acids. Included among the amides disclosed by the patent are those having the formula

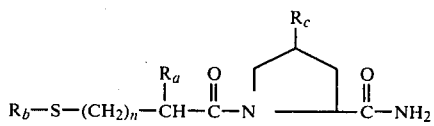

wherein n is 0, 1 or 2; $R_a$ is hydrogen or alkyl; $R_b$ is hydrogen, alkyl, phenyl, substituted phenyl, mono-, di- or tri-phenylalkyl, alkylthiomethyl, phenylalkylthiomethyl, alkanoylamidomethyl, acyl, and others; and $R_c$ is hydrogen or hydroxy.

British patent specification No. 2,014,132, published Aug. 22, 1979 discloses, inter alia, amides, N-alkylamides, and N,N-dialkylamides (wherein the alkyl group(s) can be substituted with an amino or hydroxy substituent) of certain mercaptoacyl amino acids (the mercaptoacyl side chain contains a trifluoromethyl or pentafluoroethyl substituent).

The above described compounds inhibit the conversion of angiotensin I to angiotensin II in mammals, and are, therefore, useful in the treatment of hypertension.

BRIEF DESCRIPTION OF THE INVENTION

Compounds having the formula

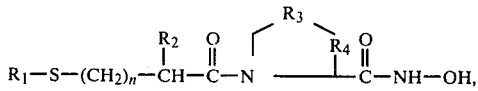   I have hypotensive activity. In formula I, and throughout the specification, the symbols are as defined below.

$R_1$ is hydrogen, alkyl, aryl, arylalkyl or a hydrolyzable acyl protecting group such as

wherein $R_5$ is alkyl or aryl;

$R_2$ is hydrogen, alkyl, trifluoromethyl or pentafluoroethyl;

$R_3$ is —CH$_2$—, —S—, —CH(OH)—, —CH(O-alkyl)—, —CH(O-aryl)—, —CH(S-alkyl)—, —CH(S-aryl)—, —C(O-alkyl)$_2$—, —C(S-alkyl)$_2$—,

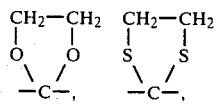

—CCl$_2$—, —CF$_2$—, —CHCl—, or —CHF— and $R_4$ is —CH$_2$— or —S—, with the proviso that if $R_4$ is —S—, $R_3$ is —CH$_2$—; or together, $R_3$ and $R_4$ can be —CH=CH; and n is 0, 1 or 2.

The term "aryl", as used throughout the specification either by itself or as part of a larger group, refers to phenyl or phenyl substituted with one, two or three halogen, alkyl, alkoxy, hydroxy,

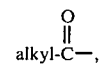

nitro, amino, alkylamino, dialkylamino, trifluoromethyl, cyano or carboxyl groups. Phenyl is the preferred aryl group.

The term "alkyl", as used throughout the specification either by itself or as part of a larger group, refers to groups having 1 to 8 carbon atoms. Alkyl groups having 1 to 3 carbon atoms are preferred.

The term "alkoxy", as used throughout the specification either by itself or as part of a larger group, refers to groups having 1 to 8 carbon atoms. Alkoxy groups having 1 to 3 groups atoms are preferred.

The term "halogen", as used throughout the specification either by itself or as part of a larger group, refers to fluorine, chlorine, bromine and iodine. The preferred halogen groups are chlorine and bromine.

DETAILED DESCRIPTION OF THE INVENTION

The compounds of formula I are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of the compounds of this invention, angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 300 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triametrene, amiloride and spironolactone and salts of such compounds.

The compounds of formula I can be formulated for use in the reduction of blood pressure in compositions such as tablets, capsules or elixirs for oral administration or in sterile solutions of suspensions for parenteral administration. About 10 to 500 mg. of a compound or mixture or compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention are readily prepared from the corresponding carboxylic acid having the formula

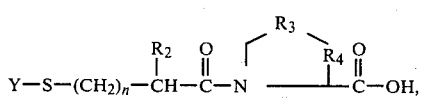

wherein Y is alkyl, aryl or a protecting group, preferably an acyl group. The conversion of an acid of formula II to the corresponding hydroxamic acid having the formula:

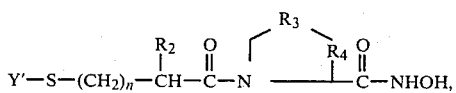

wherein Y' is alkyl, aryl or hydrogen can be accomplished by reacting the precursor acid successively with an alkyl haloformate (e.g., ethyl chloroformate) and hydroxylamine. The addition of alkyl haloformate can be carried out in the presence of an organic base (e.g., triethylamine) at a reduced temperature. The reaction can be run in an anhydrous organic solvent, preferably an ethereal solvent such as tetrahydrofuran. The subsequent reaction with hydroxylamine can likewise be run at a reduced temperature in an organic solvent, preferably a dipolar aprotic solvent such as dimethylformamide. In the products of formula III, Y' will be hydrogen if in the starting material of formula II, Y is acyl.

Those products of formula I wherein $R_1$ is a hydrolyzable acyl protecting group can be prepared from the corresponding mercapto product of formula I using art-recognized acylation techniques.

The compounds of formula II, and methods for their preparation, have been described in the patent and non-patent literature.

Those compounds of formula II wherein $R_3$ is —$CH_2$— or —CH(OH)—, $R_4$ is —$CH_2$— and $R_2$ is hydrogen or alkyl, are described in U.S. Pat. Nos. 4,046,889, issued Sept. 6, 1979; 4,105,776, issued Aug. 8, 1978; and 4,154,840, issued May 15, 1979.

Those compounds of formula II wherein $R_3$ is —$CH_2$—, —$CCl_2$—, —$CF_2$—, —CHCl—, or —CHF—, $R_4$ is —$CH_2$—, and $R_2$ is hydrogen, alkyl or trifluoromethyl are disclosed in U.S. Pat. No. 4,154,935, issued May 15, 1979.

Those compounds of formula II wherein $R_3$ and $R_4$ together are —CH=CH— and $R_2$ is hydrogen or alkyl are disclosed in U.S. Pat. Nos. 4,129,566, issued Dec. 12, 1978 and 4,154,942, issued May 15, 1979.

Those compounds of formula II wherein $R_3$ is —S— and $R_4$ is —$CH_2$— or $R_3$ is —$CH_2$— and $R_4$ is —S—, and $R_2$ is hydrogen or alkyl are disclosed in Belgian Pat. No. 861,454, issued June 2, 1978.

Those compounds of formula II wherein $R_2$ is trifluoromethyl or pentafluoroethyl and $R_3$ and $R_4$ each is —$CH_2$— or —S— or $R_3$ and $R_4$ together are —CH=CH—, are disclosed in British patent specification No. 2,014,132, published Aug. 22, 1979.

Those compounds of formula II wherein $R_3$ is —CH(O-alkyl)—, —CH(O-aryl)—, —CH(S-alkyl)—, or —CH(S-aryl)—, $R_4$ is —$CH_2$— and $R_2$ is hydrogen or alkyl are disclosed in United States patent application Ser. No. 52,691, filed July 2, 1979, the disclosure of which is incorporated herein by reference.

Those compounds of formula II wherein $R_3$ is —C(O-alkyl)$_2$—, —C(S-alkyl)$_2$—,

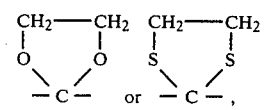

and $R_4$ is —$CH_2$— are disclosed in United States patent application Ser. No. 99,164, filed Nov. 30, 1979, the disclosure of which is incorporated herein by reference.

The products of formula I have at least one asymmetric carbon atom. If $R_2$ is other than hydrogen, the products have two asymmetric carbon atoms. The compounds, therefore, exist in stereoisomeric forms or in racemic or diastereomeric mixtures thereof. All of these are within the scope of this invention. The synthesis described above can be run using reactants that are racemic or diastereomeric mixtures or stereoisomers. When the reactants are racemic or diasteromeric mixtures, the stereoisomers of the resulting product can be separated using art-recognized techniques. The L-isomer with respect to the carbon of the amino acid constitutes the preferred isomeric form.

The following examples are specific embodiments of this invention.

EXAMPLE 1

(S)-N-Hydroxy-1-(3-mercapto-2-methyl-1-oxopropyl)-L-prolinamide

A solution of (S)-1-[3-(acetylthio)-2-methyl-1-oxopropyl]-L-proline (13.5 g, 0.05 mole) and dry, distilled, triethylamine (5.1 g, 0.05 mole) in tetrahydrofuran (250 ml) is cooled, with stirring, to −15° C. and a solution of ethyl chloroformate (5.4 g, 0.05 mole) in tetrahydrofuran (50 ml) is added dropwise as the reaction temperature is maintained at −15° C. Following the addition, stirring was continued, at −15° C., for 30 minutes. After warming to 0° C., a solution of freshly prepared hydroxylamine* (ca. 5.8 g, 0.175 mole) in dimethylformamide (230 ml) is added dropwise, at a reaction temperature of 0° C., over a period of 5 minutes. The reaction mixture is stirred at 0° C. for three hours following the addition; it is then acidified to a pH of 2 by the addition of concentrated hydrochloric acid (ca. 13 ml). After the addition of ethyl acetate (500 ml), water is added (30 ml) to effect solution of the solids still in suspension. The acidic aqueous phase is separated and extracted with ethyl acetate (two 25 ml portions). The combined organic solutions are washed with brine and dried (MgSO$_4$). After removal of the solvents in vacuo, the waxy solid residue (14 g) is triturated with ethyl acetate (50 ml), followed by trituration with acetonitrile (two 25 ml portions) to give 2.7 g of solid, melting point 145°–148° C., dec. TlC, silica gel, $CH_2Cl_2$/MeOH/HOAc (90:5:5); one spot, Rf. 0.30. (Visualized with $FeCl_3$, or nitroprusside reagent, or phosphomolybdic acid plus heat). It is recrystallized from 400 ml of ethyl acetate with a recovery of 2.1 g melting point 154°–155° C., dec. An aqueous solution shows a trace of insolubles. The solid is dissolved in 100 ml of double-distilled water, millipore filtered, and lyophilized to give 1.95 g of the title compound, melting point 154°–155° C., dec. Analysis, calc'd for $C_9H_{16}N_2O_3S \cdot \frac{1}{4} H_2O$: C, 45.64; H, 7.02; N, 11.83; S, 13.54; SH, 13.96. Found: C, 45.98; H, 7.15; N, 11.68; S, 13.16; SH, 13.66.

*The hydroxylamine solution in dimethylformamide is prepared as follows: A solution of hydroxylamine hydrochloride (12.2 g, 0.175 mole) in dry dimethylformamide (180 ml) is cooled, with stirring, to 0° C. and a solution of triethylamine (17.6 g, 0.175 mole) in dimethylformamide (50 ml) is added dropwise (10 minutes). After stirring for 5 minutes following the addition, the cold reaction mixture is rapidly filtered (minimum of suction), and the filtrate is used immediately.

EXAMPLES 2–18

Following the procedure of Example 1, but substituting the compound listed in column I for (S)-1-[3-(acetylthio)-2-methyl-1-oxopropyl]-L-proline, yields the compound listed in column II.

| | Column I | Column II |
|---|---|---|
| 2. | 1-[3-(acetylthio)-2-methyl-1-oxopropyl]-4-methoxy-L-proline | N-hydroxy-1-(3-mercapto-2-methyl-1-oxopropyl)-4-methoxy-L-prolinamide |
| 3. | 1-[3-(acetylthio)-2-methyl-1-oxopropyl]-4,4-dimethoxy-L-proline | N-hydroxy-1-(3-mercapto-2-methyl-1-oxoproyl)-4,4-dimethoxy-L-prolinamide |
| 4. | 1-[3-(acetylthio)-2-methyl-1-oxopropyl]-4-chloro-L-proline | N-hydroxy-1-(3-mercapto-2-methyl-1-oxopropyl)-4-chloro-L-prolinamide |
| 5. | 1-[3-(acetylthio)-2-methyl-1-oxopropyl]-4-fluoro-L-proline | N-hydroxy-1-(3-mercapto-2-methyl-1-oxopropyl)-4-fluoro-L-prolinamide |
| 6. | 1-[3-(acetylthio)-2-methyl-1-oxopropyl]-4,4-dichloro-L-proline | N-hydroxy-1-(3-mercapto-2-methyl-1-oxopropyl-4,4-dichloro-L-prolinamide |
| 7. | 1-[3-(acetylthio)-2-methyl-1-oxopropyl]-4,4-difluoro-L-proline | N-hydroxy-1-(3-mercapto-2-methyl-1-oxopropyl)-4,4-difluoro-L-prolinamide |
| 8. | 1-[3-(acetylthio)-2-methyl-1-oxopropyl]-4-hydroxy-L-proline | N-hydroxy-1-(3-mercapto-2-methyl-1-oxopropyl)-4-hydroxy-L-prolinamide |
| 9. | 3-[3-(acetylthio)-2-methyl-1-oxopropyl]-L-thiazolidine-4-carboxylic acid | N-hydroxy-3-(3-mercapto-2-methyl-1-oxopropyl)-L-thiazolidine-4-carboxamide |
| 10. | 3-[3-(acetylthio)-2-methyl-1-oxopropyl]-L-thiazolidine-2-carboxylic acid | N-hydroxy-3-(3-mercapto-2-methyl-1-oxopropyl)-L-thiazolidine-2-carboxamide |
| 11. | 1-[3-(acetylthio)-2-methyl-1-oxopropyl]-4,4-ethylenedioxy-L-proline | N-hydroxy-1-(3-mercapto-2-methyl-1-oxopropyl)-4,4-ethylenedioxy-L-prolinamide |
| 12. | 1-[3-(acetylthio)-2-methyl-1-oxopropyl]-4,4-ethylenedithio-L-proline | N-hydroxy-1-(3-mercapto-2-methyl-1-oxopropyl)-4,4-ethylenedithio-L-prolinamide |
| 13. | 1-[3-(acetylthio)-2-(trifluoromethyl)-1-oxopropyl]-L-proline | N-hydroxy-1-[3-mercapto-2-(trifluoromethyl)-1-oxopropyl]-L-prolinamide |
| 14. | 1-[3-(acetylthio)-2-(trifluoromethyl-1-oxopropyl]-L-3,4-dehydroproline | N-hydroxy-1-[3-mercapto-2-(trifluoromethyl)-1-oxopropyl]-L-3,4-dehydroprolinamide. |
| 15. | 1-[3-(acetylthio)-2-methyl-1-oxopropyl]-4-(methylthio)-L-proline | N-hydroxy-1-(3-mercapto-2-methyl-1-oxopropyl)-4-(methylthio)-L-prolinamide |
| 16. | 1-[3-(acetylthio)-2-methyl-1-oxopropyl]-4-(phenyloxy)-L-proline | N-hydroxy-1-(3-mercapto-2-methyl-1-oxopropyl)-4-(phenyloxy)-L-prolinamide |
| 17. | 1-[3-(acetylthio)-2-methyl-1-oxopropyl]-4-(phenylthio)-L-proline | N-hydroxy-1-(3-mercapto-2-methyl-1-oxopropyl)-4-(phenylthio)-L-prolinamide |
| 18. | 1-[3-(acetylthio)-2-methyl-1-oxopropyl]-4,4-(dimethylthio)-L-proline | N-hydroxy-1-(3-mercapto-2-methyl-1-oxopropyl)-4,4-(dimethylthio)-L-prolinamide |

What is claimed is:

1. A compound having the formula

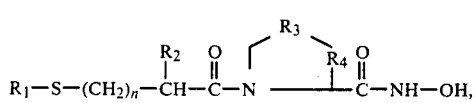

wherein $R_1$ is hydrogen, alkyl, aryl, arylalkyl or

wherein $R_5$ is alkyl or aryl;

$R_2$ is hydrogen, alkyl, trifluoromethyl or pentafluoroethyl;

$R_3$ is —$CH_2$—, —CH(OH)—, —CH(O-alkyl)—, —CH(O-aryl)—, —CH(S-alkyl), —CH(S-aryl), —C(O-alkyl)$_2$, —C(S-alkyl)$_2$,

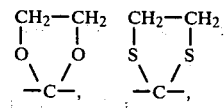

—$CCl_2$—, —$CF_2$—, —CHCl—, or —CHF— and $R_4$ is —$CH_2$; or together, $R_3$ and $R_4$ are —CH═CH—; and n is 0, 1 or 2;

wherein the term "aryl" refers to phenyl or phenyl substituted with one, two or three halogen, alkyl, alkoxy, hydroxy,

nitro, amino, alkylamino, dialkylamino, trifluoromethyl, cyano or carboxyl groups, and the terms "alkyl" and "alkoxy" refer to groups having 1 to 8 carbon atoms.

2. A compound in accordance with claim 1 wherein n is 1.

3. A compound in accordance with claim 2 wherein $R_3$ is —CH(OH)—.

4. A compound in accordance with claim 2 wherein $R_3$ is —CH(O-alkyl)—.

5. A compound in accordance with claim 4 wherein $R_3$ is —CH(OCH$_3$)—.

6. A compound in accordance with claim 2 wherein $R_3$ is —CH(O-aryl)—.

7. A compound in accordance with claim 2 wherein $R_3$ is —CH(S-alkyl)—.

8. A compound in accordance with claim 2 wherein $R_3$ is —CH(S-aryl)—.

9. A compound in accordance with claim 2 wherein $R_3$ is —C(O-alkyl)$_2$—.

10. A compound in accordance with claim 9 wherein $R_3$ is —C(OCH$_3$)$_2$—.

11. A compound in accordance with claim 2 wherein $R_3$ is —C(S-alkyl)$_2$—.

12. A compound in accordance with claim 2 wherein $R_3$ is

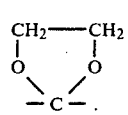

13. A compound in accordance with claim 2 wherein $R_3$ is

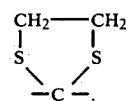

14. A compound in accordance with claim 2 wherein $R_3$ —CCl$_2$—.

15. A compound in accordance with claim 2 wherein $R_3$ is —CF$_2$—.

16. A compound in accordance with claim 2 wherein $R_3$ is —CHCl—.

17. A compound in accordance with claim 2 wherein $R_3$ is —CHF—.

18. A compound in accordance with claim 2 wherein $R_3$ and $R_4$ are together —CH=CH—.

19. The compound in accordance with claim 1 (S)-N-hydroxy-1-(3-mercapto-2-methyl-1-oxopropyl)-L-prolinamide.

* * * * *

UNITED STATES PATENT AND TRADEMARK OFFICE
CERTIFICATE OF CORRECTION

PATENT NO. : 4,284,561
DATED : August 18, 1981
INVENTOR(S) : Edward W. Petrillo, Jr., et al.

It is certified that error appears in the above—identified patent and that said Letters Patent is hereby corrected as shown below:

Column 2, line 18, delete the word "groups" and add --carbon-- in its place.

Column 3, line 2, "triamterene" is misspelled.

Signed and Sealed this

Third Day of November 1981

[SEAL]

Attest:

GERALD J. MOSSINGHOFF

Attesting Officer    Commissioner of Patents and Trademarks